United States Patent [19]

Karpinski et al.

[11] Patent Number: 5,731,477
[45] Date of Patent: Mar. 24, 1998

[54] METHOD FOR SYNTHESIS OF ARYL DIFLUOROMETHYL ETHERS

[75] Inventors: Joseph M. Karpinski, Pottstown; Siegfried B. Christensen, IV, Philadelphia, both of Pa.; Steven Dabbs, Harlow Essex, United Kingdom

[73] Assignee: SmithKline Beecham Corporation, Phila, Pa.

[21] Appl. No.: 381,165

[22] Filed: Jan. 31, 1995

[51] Int. Cl.$^6$ .................................................... C07C 49/76
[52] U.S. Cl. ............................ 568/663; 568/56; 548/469
[58] Field of Search ..................... 568/56, 663; 548/469

[56] References Cited

FOREIGN PATENT DOCUMENTS

A 59-15704  9/1984  Japan .

OTHER PUBLICATIONS

Poludnenko et al; Zh.Org.Khim.;20(11),p. 2483, 1984.

Hendrickson et al; Third Edition; p. 544; lines 1–9, 1970.

*Primary Examiner*—Gary Geist
*Assistant Examiner*—Sreeni Padmanabhan
*Attorney, Agent, or Firm*—James M. Kanagy; Stephen Venetianer; Edward T. Lentz

[57] ABSTRACT

This invention relates to a method for preparing difluoromethyl ethers, thiols and amines without using chlorofluorocarbon gases. The intermediates prepared by this method can be used to make certain compounds which act as PDE IV inhibitors which are useful for treating asthma and other diseases implicated with the PDE IV isozyme.

16 Claims, No Drawings

METHOD FOR SYNTHESIS OF ARYL DIFLUOROMETHYL ETHERS

SCOPE OF THE INVENTION

This invention relates to a method for preparing difluoromethyl ethers, thioethers and amines without using chlorofluorocarbon gases. The intermediates prepared by this method can be used to make certain compounds which act as PDE IV inhibitors which are useful for treating asthma and other diseases implicated with the PDE IV isozyme.

BACKGROUND OF THE INVENTION

Difluoromethoxyaromatic compounds can be prepared by using chlorofluorocarbon gases. But with the reduction in production of CFC in light of the impending ban on these compounds because of ozone layer depletion concerns, alternative methods for synthesizing fluorine-containing hydrocarbons are needed. This invention provides one such method. It is illustrated in the context of the preparation of certain PDE IV inhibitors.

By way of background, bronchial asthma is a complex, multifactorial disease characterized by reversible narrowing of the airway and hyperactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophospate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over Agents currently on the market.

Compounds which inhibit the PDE IV isozyme and which are prepared using the intermediates made by the process of this invention are disclosed and claimed in certain co-pending U.S. applications, including but not limited to the following set of co-pending applications: USSN 08/313092 arising from PCT application PCT/93US/01990 (WO 93/19748); USSN 08/313095 arising from PCT application number PCT/US93/02325 (WO 93/19750); USSN 08/313093 arising from PCT application number PCT/US93/02516 (WO 93/19751); USSN 08/313096 arising from PCT application number PCT/US93/01988 (WO 93/19747); USSN 08/313094 derived from PCT/US93/01991 (WO 93/19749), and USSN 08/313097 derived from PCT application number PCT/US93/02230 (WO 93/19720). Those applications are incorporated herein by reference.

These are but some examples of end products which can be made using the intermediates resulting from the new method presented herein for making difluoromethoxy aromatic compounds, etc.

SUMMARY OF THE INVENTION

This invention relates to a method for preparing difluoromethyl aromatic compounds of formula 1:

$$R—X—CF_2H \qquad (I)$$

where R is unsubstituted or substituted phenyl, pyridyl, or naphthyl; which process comprises treating a compound of formula II $$RXH \qquad (II)$$

where X is O, S or NH
with an excess of an alkali metal salt of $YCF_2C(O)O$— where Y is Br, Cl or I in a solvent selected from the group consisting of dimethyl formamide, N-methylmorpholine, dimethylsulfoxide or N-methylpyrrolidinone in the presence of an inorganic base in a molar amount essentially equal to the haloacetate moiety at a temperature between about 100° to 150° C. for 1 to 10 hours; or treating said compound with an excess of a $C_1$ to $C_6$alkyl ester of $YCF_2C(O)O$— where Y is Br, Cl or I in a solvent selected from the group consisting of dimethyl formamide, N-methylmorpholine, dimethylsulfoxide or N-methylpyrrolidinone in the presence of an inorganic base in a molar amount essentially equal to the haloacetate moiety at a temperature between about 50° to 100° C. for 0.1 to 5 hours.

In another aspect, this invention can be used to difluoromethylate the nitrogen of indoles, which process comprises treating the indole anion with an excess of an alkali metal salt of $YCF_2C(O)O$— or the $C_1$ to $C_6$alkyl ester of $YCF_2C(O)$— where Y is Br, Cl or I in a solvent selected from the group consisting of dimethyl formamide, N-methylmorpholine, dimethylsulfoxide or N-methylpyrrolidinone, in the presence of an inorganic base in a molar amount essentially equal to the acetate moiety, at a temperature between about 50° and 150° C. for 0.1 to 10 hours.

DESCRIPTION OF THE INVENTION

In the most general embodiment, this invention can be used to convert aromatic phenols and the like which can act as nucleophile, to the corresponding difluoromethoxy, difluoromethylthiol or difluoromethylamine. The invention can also be utililized in the case to difluoromethylate ring nitrogens. This case is illustrated by the heteroaromatic bicyclic indoles and similar compounds which comprise two rings, one being an aryl ring and the other containing a nitrogen atom which can act as a nuclcophile. This chemistry could also be used to synthesize the likes of difluoromethyl alkanoates, difluoromethyl alkanesulfonates, alkyl difluoromethyl ethers and alkyl difluoromethyl thioethers.

The source of the difluoromethyl group which is added is the alkali metal salt or ester of halodifluoroacetate. These salts and esters are readily available from fine chemical houses or can be prepared by literature methods. The preferred salt is the sodium salt. The preferred ester is the methyl ester. As regards the 'halo' group on the acetate, it must be something other that fluorine. While it is preferred that one use the chlorodifluoroacetate compound, the corresponding bromodifluoroacetates and iodododifluoroacetates can be used as well.

The amount of acetate used will be some amount which represents a molar excess of the acetate over that of the substrate, the phenol for example. While the reaction will proceed if less than an excess of acetate is used, obviously the reaction will not go to completion in the sense that the substrate phenol will all be reacted. It is preferred to use at least about a 10% excess of the acetate up to about a 100% excess, particularly as applied to the alkyl haloacetates. These ranges use molar concentrations as the comparative measure. As for preferred ranges of concentrations, for the alkali metal salts a 10 to 30% excess is preferred. For the alkyl ester, a 50 to 100% excess is preferred.

Solvents useful in this invention are non-protic polar solvents. Examples of such useful solvents are dimethyl formamide, N-methylmorpholine, dimethylsulfoxide, N-methylpyrrolidinone and the like. Dry solvents should be used. An inert atmosphere should be maintained in the reaction vessel throughout the course of the reaction.

The inorganic bases which can be used in this invention are the water soluble alkali metal hydroxides such as sodium hydroxide and potassium hydroxide. Other inorganic bases such as the alkali metal carbonates such as $Na_2CO_3$ or $K_2CO_3$. The base concentration will be somewhere around the same molar concentration as that of the halodifluoroacetate. For example if the substrate phenol is present at a concentration of 0.8 mmol and the haloacetate is an alkali metal salt at a 10 to 30% excess, then the base will be used at a 10 to 30% excess. If the haloacetate is an alkyl ester and is used at a 100% excess, then the base likewise will be present at an excess of 100% relative to the substrate.

A novel factor in this reaction is the low and relatively narrow temperature range in which this difluoromethylation can be made to run. With the combination of reactants and solvents recited above, this reaction can be made to proceed in several hours at temperatures ranging between 50° and 150° C. inclusive, for both the alkali metal salt form and the alkyl ester form of the haloacetate. There is a distinction in the preferred temperature ranges however as between the alkali metal salt form and the alkyl ester form. The reaction should be run at between 100° and 150° C. when one is using an alkali metal salt as the source of difluoromethyl carbene intermediate. But the reaction can be run at 50° to 100° C. If the alkyl ester form of the haloacetate is used.

The time in which this reaction will go to completion will depend in part on the temperature at which the reaction is carded out and the reactants being used. A general range is from about 10 minutes to 10 hours. This range encompasses full the scope of all combination of substrates, reactants and temperatures. Keeping these factors in mind, it is expected that reactions can be run in a time of between about 5 minutes to 10 hours. The time element, as with the temperature element has been found to vary depending on which form of the haloacetate is used, the salt versus the alkyl ester. For example 4-cyanophenol is converted to 4-difluoromethoxybenzonitrile in about 5 hours using the salt form, i.e. sodium chlorodifluoroacetate and sodium hydroxide. But if the difluoromethyl carbene source is the methyl ester, for example, the 4-cyanophenol conversion is complete in about 20 minutes. Similarly when 4-nitrophenol was used as the substrate the reaction ran its course in about 1 hour using the sodium salt and in 30 minutes using the methyl ester. However this phenomenon did not repeat itself for the 3,4-dihydroxybenzaldehyde. There the sodium salt went to completion in about 1 hour (at 125° C.) while the methyl ester chlorodifluoroacetate required 3 hours (at 60°–65° C.) to go to completion.

As regards the use of these difluoromethoxy intermediates, the disclosure in PCT application PCT/US93/01991 (WO93/19749) has in its general structure a difluoromethoxy substituent on a benzene ring. A preferred subgenus of the compounds of is that disclosure is the compounds of the Formula (Ia)

wherein:

$R_1$ is $CH_2$-cyclopropyl, $CH_2$–$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}C(O)O(CH_2)_{0-2}CH_3$, —$(CH_2)_{1-3}(CH_2)_{0-2}CH_3$, and —$(CH_2)_{2-4}OH$;

X is (among other radicals) $YR_2$ where Y is O and $R_2$ is $C_{1-4}$ alkyl optionally substituted by one to three fluorines;

$X_4$ is

or

the Z, $X_5$ and $R_3$ radicals being fully defined in the referenced writing. Methods for preparing these preferred compounds are disclosed in that publication as well. Hence, for example, the difluoromethoxy compounds made by the processes provided in this invention can be used to make the following compounds methyl cis-[4-(3,4-bisdifluoromethoxyphenyl)-4-cyanocyclohexane-1-carboxylate];

methyl trans-[4-(3,4-bisdifluoromethoxyphenyl)-4-cyanocyclohexane-1-carboxylate];

cis-[4-(3,4-bisdifluoromethoxyphenyl)-4-cyanocyclohexane-1-carboxylic acid];

methyl cis-[4-cyano-4-(3-cyclopropylmethoxy-4-difluoromethoxyphenyl)cyclohexane-1-carboxylate];

methyl trans-[4-cyano-4-(3-cyclopropylmethoxy-4-difluoromethoxyphenyl)-cyclohexane-1-carboxylate];

cis-[4-cyano-4-(3-cyclopropylmethoxy-4-difluoromethoxyphenyl)cyclohexane-1-carboxylic acid];

trans-[4-cyano-4-(3-cyclopropylmethoxy-4-difluoromethoxyphenyl)cyclohexane-1-carboxylic acid]; and the like.

These compounds are useful for treating asthma and other diseases related to PDE IV as more fully set forth in the referenced publications.

The following examples are given to illustrate the invention. These examples are not intended to and should not be read to limit the scope of the invention in any manner or in any context.

SPECIFIC EMBODIMENTS

Compounds of Formula 1 wherein R is substituted phenyl are prepared by methods analogous to those described in Scheme 1.

Scheme 1

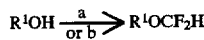

$R^1$ is any aromatic group.
a) $ClCF_2CO_2^-Na^+$, DMF, NaOH
b) $ClCF_2CO_2CH_3$, DMF, $K_2CO_3$

EXAMPLE 1

Preparation of 4-difluoromethoxybenzonitrile

4-Cyanophenol (0.50 g, 4.2 mmol, Aldrich), sodium chlorodifluoroacetate (0.77 g, 5 mmol, Alfa Products), and sodium hydroxide (0.20 g, 5 mmol) were combined in dry DMF (2 mL) under an atmosphere of argon. After stirring at 125°–130° C. for 5 h, the mixture was cooled to RT, ethyl acetate (50 mL) was added and the organic layer was washed twice with brine. The organic extract was dried ($MgSO_4$), filtered and evaporated. The residue was purified by flash chromatography (silica gel, 25% ethyl acetate/hexanes) to provide a white solid. The solid was sublimed (1 mm Hg, 23° C.) to provide the title compound as colorless crystals (0.29 g, 41%). mp 33°–35° C.

EXAMPLE 2

Preparation of 3-difluoromethoxybenzonitrile

Following the procedure of Example 1, except substituting 3-cyanophenol (Aldrich) for 4-cyanophenol and purification by flash chromatography (silica gel, 20% ether/hexanes), the title compound was prepared as a clear liquid (0.29 g, 41%). MS(CI/$NH_3$) m/e 187 [M+$NH_4$].

EXAMPLE 3

Preparation of 4-difluoromethoxynitrobenzene

4-Nitrophenol (0.10 g, 0.72 mmol, Aldrich), sodium chlorodifluoroacetate (0.11 g, 0.72 mmol, Alfa Products) and sodium hydroxide (0.03 g, 0.72 mmol) were combined in dry DMF (1 mL) under an atmosphere of argon. After stirring at 125° C. for 1 h, the mixture was cooled to RT, was diluted with water and was extracted twice with ether. The combined organic extracts were washed twice with brine, were dried ($MgSO_4$), filtered and evaporated. The residue was purified by flash chromatography (silica gel, 25% ethyl acetate/hexanes) to provide the title compound as a white solid (0.10 g, 73%). mp 33°–35° C.

EXAMPLE 4

Preparation of 3-difluoromethoxynitrobenzene

Following the procedure of Example 3, except substituting 3-nitrophenol (Aldrich) for 4-nitrophenol and purification by flash chromatography (silica gel, 16% ether/hexanes), the title compound was prepared as a clear, yellow liquid (0.41 g, 60% ). MS(CI/$NH_3$) m/e 207 [M+$NH_4$].

EXAMPLE 5

Preparation of 4-difluoromethoxy-3-hydroxybenzaldedye 3,4-Dihydroxybenzaldehyde (0.50 g, 3.62 mmol, Aldrich), sodium chlorodifluoroacetate (0.55 g, 3.62 mmol, Alfa Products) and sodium hydroxide (0.145 g, 3.62 mmol) were combined in dry DMF (5 mL) and water (0.07 mL) under an argon atmosphere. After stirring at 125° C. for 1 hr, DMF was removed in vacuo and the residue was partitioned between aqueous 3N HCl and ether. The aqueous layer was extracted three times with ether. The combined organic extracts were washed with water, with brine, were dried ($MgSO_4$), filtered and evaporated. The residue was purified by flash chromatography (silica gel, 25% ethyl acetate/hexanes) to provide the title compound as a white solid (0.32 g, 47%). mp 83°–85° C.

EXAMPLE 6

Preparation of 4-difluoromethoxybenzonitrile

4-Cyanophenol (0.12 G, 1.0 mmol, Aldrich), methyl chlorodifluoroacetate (0.29 g, 2.0 mmol, Aldrich) and potassium carbonate (0.29 g, 2.1 mmol) were combined in dry DMF (0.5 mL) under an argon atmosphere. After stirring at 75°–80° C. for 0.3 h, the mixture was cooled to RT, ethyl acetate (20 mL) was added and the organic layer was washed twice with 10% NaOH. The organic extract was dried ($MgSO_4$), filtered and evaporated. The residue was purified by flash chromatography (silica gel, 20% ether/hexanes) to provide the title compound as a colorless solid (0.09 g, 53%). mp 34°–35° C.

EXAMPLE 7

Preparation of 3-difluoromethoxybenzonitrile

Following the procedure of Example 6, except substituting 3-cyanophenol (Aldrich) for 4-cyanophenol, the title compound was prepared as a clear liquid (0.08 g, 47%). MS(CI/$NH_3$) m/e 187 [M+$NH_4$].

EXAMPLE 8

Preparation of 4-difluoromethoxynitrobenzene

4-Nitrophenol (0.14 g, 1.0 mmol, Aldrich), methyl chlorodifluoroacetate (0.29 g, 2.0 mmol, Aldrich) and potassium carbonate (0.29 g, 2.1 mmol) were combined in dry DMF (0.5 mL) under an argon atmosphere. After stirring at 95°–100° C. for 0.5 h, the mixture was cooled to RT, ethyl acetate (20 mL) was added and the organic layer was washed three times with 10% NaOH. The organic extract was dried ($MgSO_4$), filtered and evaporated. The residue was purified by flash chromatography (silica gel, 20% ether/hexanes) to provide the title compound as a white solid (0.12 g, 65%). mp 33°–35° C.

EXAMPLE 9

Preparation of 3-difluoromethoxynitrobenzene

Following the procedure of Example 8, except substituting 3-nitrophenol (Aldrich) for 4-nitrophenol, the title compound was prepared as a clear, yellow liquid (0.1 g, 53%). MS(CI/NH$_3$) m/e 207 [M+NH$_4$].

EXAMPLE 10

Preparation of 4-difluoromethoxy-3-hydroxybenzaldehyde 3,4-Dihydroxybenzaldehyde (0.50 g, 3.62 mmol, Aldrich), methyl chlorodifluoroacetate (0.52 g, 3.62 mmol, Aldrich) and potassium carbonate (0.50 g, 3.62 mmol) were combined in DMF (5.0 mL) under an argon atmosphere. After stirring at 60°–65° C. for 3 h, DMF was removed in vacuo and the residue was partioned between aqueous 3N HCl and ether. The aqueous layer was extracted three times with ether. The combined organic extracts were washed with water, with brine, were dried (MgSO$_4$), filtered and evaporated. The residue was purified by flash chromatography (silica gel, 25% ethyl acetate/hexanes) to provide the title compound as a white solid (0.20 g, 38%). mp 83°–85° C.

EXAMPLE 11

1-Acetyl-6-bromo-5-difluoromethoxyindoline

1-Acetyl-6-bromo-5-hydroxyindoline (2 g, 7.8 mmol), methyl 2-chloro-2,2-difluoroacetate (0.82 ml, 7.8 mmol) and potassium carbonate (1.08 g, 7.8 mmol) were suspended in N,N-dimethylformamide (20 mL) under an argon atmosphere and placed in a 65° C. oil bath. After 3 hr, additional methyl 2-chloro-2,2-difluoroacetate (0.3 ml, 2.8 mmol) and potassium carbonate (0.3 g, 2.2 mmol) was added and heated for 18 hr. The solvent was then removed in vacuo and the residue was partitioned between cold 3N HCl and ether. The aqueous layer was extracted three times with ether, the combined organic extracts were washed with brine, dried (Na$_2$SO$_4$), filtered and evaporated. The solid was purified by flash chromatography (2% MeOH/CH$_2$Cl$_2$) to provide the title compound as a white solid $^1$H NMR (250 MHz) CDCl$_3$ (and a few drops of d$_6$-DMSO): δ: 8.03 (s; 1H), 6.7 (s, 1H), 6.2 (t, 1H), 3.75 (t, 2H), 2.80 (t, 2H), 1.87 (s, 3H).

EXAMPLE 12

1-Acetyl-2,3-dihydro-5-difluoromethylpyrrolo-[2,3-f]indole

Sodium hydride (80% dispersion in mineral oil) (0.036 g, 11.2 mmoles) was added to a solution of 1-acetyl-2,3-dihydropyrrolo[2,3-f]indole (0.2 g, 1.0 mmoles) in dry dimethylformamide (3.0 ml) at ambient temperature. After 30 mins, methyl 2-chloro-2,2-difluoroacetate (0.13 mL, 1.2 mmol) was added and the mixture heated to 60° C. for 3 hrs. The mixture was concentrated in vacuo and the residue partitioned between 2N hydrochloric acid and dichloromethane. The organic layer was separated, dried over anhydrous sodium sulphate, filtered and evaporated to dryness. This gave approximately 0.2 g of a crude mixture. Mass spectral evidence indicated the presence of the title compound as part of a complex mixture.

Found: M$^+$250(trace); C$_{13}$H$_{12}$F$_2$N$_2$O requires 250.

What is claimed is:

1. A method for preparing difluoromethyl aromatic compounds of formula 1:

R—X—CF$_2$H (I)

where R is unsubstituted or substituted phenyl, pyridyl, or naphthyl; which process comprises treating a compound formula II

RXH (II)

where X is O, S or NH with an excess of an alkali metal salt of YCF$_2$C(O)O— where Y is Br, Cl or I in a solvent selected from the group consisting of dimethyl formamide, N-methylmorpholine, dimethylsulfoxide and N-methylpyrrolidinone in the presence of an inorganic base in a molar amount essentially equal to the haloacetate moiety at a temperature between about 100° to 150° C. for 1 to 10 hours.

2. A method for preparing difluoromethyl aromatic compounds of formula 1:

R—X—CF$_2$H (I)

where R is unsubstituted or substituted phenyl, pyridyl, or naphthyl; which process comprises treating a compound formula II

RXH (II)

where X is O, S or NH with and excess of a C$_1$ to C$_6$alkyl ester of YCF$_2$C(O)O— where Y is Br, Cl or I in a solvent selected from the group consisting of dimethyl formamide, N-methylmorpholine, dimethylsulfoxide and N-methylpyrrolidinone in the presence of an inorganic base in a molar amount essentially equal to the haloacetate moiety at a temperature between about 50° to 100° C. for 0.1 to 5 hours.

3. A method for difluoromethylating the nitrogen of indoles which method comprises treating the indole with an excess of an alkali metal salt of YCF$_2$C(O)O— or the C$_1$ to C$_6$alkyl ester of YCF$_2$C(O)— where Y is Br, Cl or I in a solvent selected from the group consisting of dimethyl formamide, N-methylmorpholine, dimethylsulfoxide and N-methylpyrrolidinone, in the presence of an inorganic base in a molar amount essentially equal to the acetate moiety, at a temperature between about 50° and 150° C. for 0.1 to 10 hours.

4. The method of claim 1 wherein R is substituted phenyl, X is O and the inorganic base is an alkali metal hydroxide or an alkali metal carbonate.

5. The method of claim 4 wherein R is 3,4-dihydroxybenzaldehyde, 3- or 4-nitrophenol, or 3- or 4-cyanophenol; the haloacetate is sodium chlorodifluoroacetate; and the base is sodium hydroxide.

6. The method of claim 4 wherein the acetate is present in about a 10 to 30% molar excess.

7. The method of claim 5 wherein the acetate is present in about a 10 to 30% molar excess.

8. The method of claim 2 wherein R is a substituted phenyl, X is O and the inorganic base is an alkali metal hydroxide or an alkali metal carbonate.

9. The method of claim 8 wherein R is 3- or 4-cyanophenol, 3- or 4-nitrophenol, or 3,4-dihydroxybenzaldehyde; the haloacetate moiety is methyl chlorodifluoroacetate; and the base is potassium carbonate.

10. The method of claim 8 wherein the haloacetate is about a 50 to 100% molar.

11. The method of claim 9 wherein the haloacetate is about a 50 to 100% molar excess.

12. The method of claim 3 wherein the indole is 1-acetyl-6-bromo-5-hydroxyindoline, the acetate is methyl 2-chloro-2,2-difluoroacetate, and the base is potassium carbonate.

13. The method of claim 12 wherein the haloacetate is about a 50 to 100% molar excess.

14. A method for preparing difluoromethyl aromatic compounds of formula 1:

$$R-X-CF_2H \quad (I)$$

where R is unsubstituted or substituted phenyl, pyridyl, or naphthyl; which process comprises treating a compound formula II $$RXH \quad (II)$$

where X is O, S or NH
with au excess of an alkali metal salt of $YCF_2C(O)O-$ where Y is Br, Cl or I in a polar non-protic solvent in the presence of an inorganic base in a molar amount essentially equal to the haloacetate moiety at a temperature between about 100° to 150° C. for 1 to 10 hours.

15. A method for preparing difluoromethyl aromatic compounds of formula 1:

$$R-X-CF_2H \quad (I)$$

where R is unsubstituted or substituted phenyl, pyridyl, or naphthyl; which process comprises treating a compound formula II $$RXH \quad (II)$$

where X is O, S or NH
with and excess of a $C_1$ to $C_6$ alkyl ester of $YCF_2C(O)O-$ where Y is Br, Cl or I in a polar non-protic solvent in the presence of an inorganic base in a molar amount essentially equal to the haloacetate moiety at a temperature between about 50° to 100° C. for 0.1 to 5 hours.

16. A method for difluoromethylating the nitrogen of indoles which method comprises treating the indole with an excess of an alkali metal salt of $YCF_2C(O)O-$ or the $C_1$ to $C_6$ alkyl ester of $YCF_2C(O)-$ where Y is Br, Cl or I in a polar non-protic solvent in the presence of an inorganic base in a molar mount essentially equal to the acetate moiety, at a temperature between about 50° and 150° C. for 0.1 to 10 hours.

* * * * *